United States Patent [19]

Nordmann et al.

[11] Patent Number: 4,565,818
[45] Date of Patent: Jan. 21, 1986

[54] PHARMACEUTICALLY ACTIVE 1,2,3,4,4A,5,10,10A-OCTAHYDRO-BENZO[G-]QUINOLINE DERIVATIVES

[75] Inventors: René Nordmann, Basel; Trevor J. Petcher, Binningen, both of Switzerland

[73] Assignee: Sandoz Ltd., Basel, Switzerland

[21] Appl. No.: 434,202

[22] Filed: Oct. 14, 1982

[30] Foreign Application Priority Data

Oct. 16, 1981 [CH] Switzerland ............... 6631/81
Jun. 25, 1982 [CH] Switzerland ............... 3927/81

[51] Int. Cl.$^4$ ............... C07D 221/08; C07D 401/12; C07D 401/06; A61K 31/435
[52] U.S. Cl. ............... 514/290; 514/239; 546/101; 544/126; 560/35; 560/45; 560/10; 560/53
[58] Field of Search ............... 546/101; 424/258, 248, 424/57; 544/126

[56] References Cited

U.S. PATENT DOCUMENTS 3,839,338 10/1974 Albertson et al. ............ 424/258 X
4,100,164  7/1978 Michne ..................... 424/258 X
4,235,909 11/1980 Bach et al. .................... 424/258

OTHER PUBLICATIONS

Bach et al., II, *J. Med. Chem.* 23, 481–91 (1980).
Cannon et al., *J. Med. Chem.* 23 (1), 1–5 (1980).
Cannon et al., *Med. Chem. Advances*, 369–381, Pergamon Press, 1981.
Cannon et al., *J. Heterocyclic Chem.* 17, 1633–1636 (1980).
Walsh, et al., *J. Org. Chem.* 39 (25), 3705–3708 (1974).

*Primary Examiner*—Mark L. Berch
*Attorney, Agent, or Firm*—Gerald D. Sharkin; Robert S. Honor; Thomas O. McGovern

[57] ABSTRACT

A 6- and/or 7-oxy-trans-1,2,3,4,4a,5,10,10a-octahydrobenzo[g]quinoline in which the 3-position is substituted by an optionally amidated carboxy group, an optionally etherified hydroxymethyl group, a cyanomethyl group, an alkyl- or aryl-thiomethyl group or a sulfamoylamino or carbamoylamino group, or a physiologically-hydrolysable and -acceptable ester thereof. The subject compounds are useful as pharmaceuticals, in particular as prolactin secretion inhibitors, dopaminergic agents ad dopamine receptor stimulating agents.

16 Claims, No Drawings

PHARMACEUTICALLY ACTIVE 1,2,3,4,4A,5,10,10A-OCTAHYDRO-BENZO[G]QUINOLINE DERIVATIVES

The present invention relates to novel 1,2,3,4,4a,5,10,10a-octahydro-benzo[g]quinoline derivatives having valuable pharmaceutical properties, processes for the production of said derivatives, pharmaceutical compositions comprising said derivatives and the use of said derivatives as pharmaceuticals.

More particularly the present invention provides a 6- and/or 7-oxy-trans-1,2,3,4,4a,5,10,10a-octahydro-benzo[g]quinoline in which the 3-position is substituted by an optionally amidated carboxy group, an optionally etherified hydroxymethyl group, a cyanomethyl group, an alkyl- or aryl-thiomethyl group or a sulfamoylamino or carbamoylamino group, or a physiologically-hydrolysable and -acceptable ester thereof.

The benzo[g]quinoline nucleus of the compounds in accordance with the invention may bear further substituents, i.e. in addition to those defined above at the 6- and/or 7- and 3-positions. Preferred benzo[g]quinolines in accordance with the invention are those in which the 1-position is unsubstituted or is substituted by a $C_{1-4}$alkyl group. Suitably no further substituents other than $C_{1-4}$alkyl at the 1-position are present.

The term "aryl" as applied to aryl-thio methyl groups which may be present at the 3-position includes heteroaryl moieties such as pyridyl. Preferred substituents at the 6- and/or 7-position are hydroxy and methoxy. Preferred substituents at the 3-position are substituents $R_4$ as defined below.

Especially preferred in accordance with the present invention are benzo[g]quinolines of formula I,

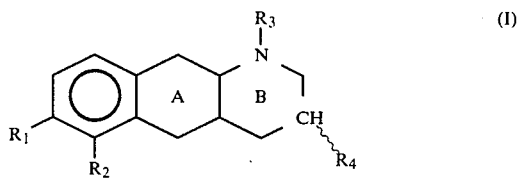

wherein
the rings A and B are trans-fused and wherein
$R_1$ and $R_2$ are each independently hydrogen, hydroxy or methoxy, with the proviso that $R_1$ and $R_2$ may not both be hydrogen;
$R_3$ is hydrogen or $C_{1-4}$alkyl;
$R_4$ is —COOH, —CH$_2$OR$_5$, —CH$_2$CN, —CON(R$_6$)R$_7$, —CH$_2$SR$_8$, —NHSO$_2$N(R$_9$)R$_{10}$ or —NHCON(R$_9$)R$_{10}$,
$R_5$ is hydrogen or $C_{1-3}$alkyl,
$R_6$ is hydrogen or $C_{1-3}$alkyl and
$R_7$ is hydrogen, $C_{1-3}$alkyl, phenyl or pyridyl, said phenyl or pyridyl being optionally substituted by halogen, methyl or methoxy or
$R_6$ and $R_7$ together are —(CH$_2$)$_4$—, —(CH$_2$)$_5$— or —(CH$_2$)$_2$—O—(CH$_2$)$_2$—,
$R_8$ is $C_{1-4}$alkyl or pyridyl, said pyridyl being optionally substituted by halogen, methyl or methoxy, and
$R_9$ and $R_{10}$ are each independently hydrogen or $C_{1-3}$alkyl or together are —(CH$_2$)$_4$— or —(CH$_2$)$_5$—,
as well as the physiologically-hydrolysable and -acceptable esters thereof.

"Halogen" as used herein means fluorine, chlorine or bromine. "Pyridyl" includes 2-, 3- and 4-pyridyl. By the term "physiologically-hydrolysable and -acceptable esters" is meant esters with acids or alcohols which are hydrolysable under physiological conditions to yield acids and alcohols which are themselves physiologically acceptable, i.e. which are non-toxic at the desired dosage levels. Such esters may be obtained by acylation of benzo[g]quinolines in accordance with the invention bearing one or more hydroxy residues, e.g. hydroxy and/or hydroxymethyl groups at the 3-, 6- and/or 7-position and/or esterification of benzo[g]quinolines in accordance with the invention bearing an acidic residue, e.g. a carboxy group at the 3-position. Such esters include esters with mono- and di-carboxylic acids in particular carboxylic acids having 2 to 5 carbon atoms, as well as esters with aliphatic alcohols having 1 to 4 carbon atoms.

In formula I the following significances as well as combinations thereof are preferred:
1. $R_1$ and $R_2$ are independently hydrogen or hydroxy. Most preferably one is hydrogen and the other is hydroxy.
2. $R_3$ is $C_{1-4}$alkyl, especially n-propyl.
3. $R_4$ is other than —COOH; and is especially —CON(R$_6$)R$_7$, —CH$_2$SR$_8$, —NHSO$_2$N(R$_9$)R$_{10}$ or —NHCON(R$_9$)R$_{10}$, more especially —CH$_2$SR$_8$ or —NHSO$_2$N(R$_9$)R$_{10}$, most especially —NHSO$_2$N(R$_9$)R$_{10}$.
4. $R_5$ is hydrogen.
5. $R_6$ is hydrogen and $R_7$ is pyridyl optionally substituted by halogen, methyl or methoxy; especially pyridyl optionally mono-substituted by halogen, methyl or methoxy; more especially 3-pyridyl mono-substituted in the paraposition by methoxy.
6. $R_8$ is $C_{1-4}$alkyl, especially methyl.
7. $R_9$ is hydrogen or $C_{1-4}$alkyl; especially $C_{1-4}$alkyl; in particular ethyl, and $R_{10}$ is hydrogen or $C_{1-4}$alkyl; especially $C_{1-4}$alkyl; in particular ethyl.

One group of compounds in accordance with the present invention comprises benzo[g]quinolines of formula I as illustrated above,
wherein
$R_1$ and $R_2$ are both hydroxy or both methoxy or one of $R_1$ and $R_2$ is hydrogen and the other is hydroxy or methoxy,
$R_3$ is $C_{1-4}$alkyl,
$R_4$ is —CH$_2$OH, —CH$_2$CN, —CON(R$_6$)R$_7$, —CH$_2$SR$_8$, —NHSO$_2$N(R$_9$)R$_{10}$ or —NHCON(R$_9$)R$_{10}$,
$R_6$ is hydrogen or $C_{1-3}$alkyl,
$R_7$ is pyridyl optionally substituted by halogen, methyl or methoxy and
$R_8$, $R_9$ and $R_{10}$ have the meanings given for formula I, as well as the physiologically-hydrolysable and -acceptable esters thereof.

A second group of compounds in accordance with the present invention comprises benzo[g]quinolines of formula I as illustrated above,
wherein
$R_1$, $R_2$ and $R_3$ have the meanings given for formula I,
$R_4$ is —COOH, —CH$_2$OH, —CH$_2$CN, —CON(R$_6$)R$_7$, —CH$_2$SR$_8$, —NHSO$_2$N(R$_9$)R$_{10}$ or —NHCON(R$_9$)R$_{10}$, and
$R_6$, $R_7$, $R_8$, $R_9$ and $R_{10}$ have the meanings given for formula I,
as well as the physiologically-hydrolysable and -acceptable esters thereof.

A further group of compounds in accordance with the present invention comprises benzo[g]quinolines of formula I as illustrated above, wherein one of $R_1$ and $R_2$ is hydrogen and the other is hydroxy or methoxy, and $R_3$ through $R_{10}$ have the meanings given for formula I, as well as the physiologically-hydrolysable and -acceptable esters thereof.

The compounds of the present invention exist in free and in salt form, e.g. as acid addition salts or, when e.g. $R_4$ is carboxy, as salts with bases. The present invention includes both free and salt, in particular pharmaceutically acceptable salt, forms. Examples of appropriate pharmaceutically acceptable acid addition salt forms include e.g. the hydrochlorides and maleates. Pharmaceutically acceptable salts with bases include e.g. the sodium salts.

The substituent at the 3-position of the benzo[g]quinoline nucleus of the compounds of the invention ($R_4$ in formula I) may be in the α- or β-position. Since the nucleus has the trans-configuration (i.e. the rings A and B in formula I are trans-fused, whereby hydrogen atoms at the 4a- and 10a-positions are also trans to each other) the compounds of the invention exist in four isomeric forms comprising two enantiomeric pairs. Where further substituents are present or where substituents themselves contain optically active centres, further isomeric forms will exist. It will be understood that the present invention includes both individual isomers, as well as racemates (i.e. mixtures comprising a single enantiomeric isomer pair) and other isomeric mixtures.

For formula I, the only optically active centres present in the nucleus are at positions 3, 4a and 10a, giving 4 isomeric forms. These may be represented as follows:

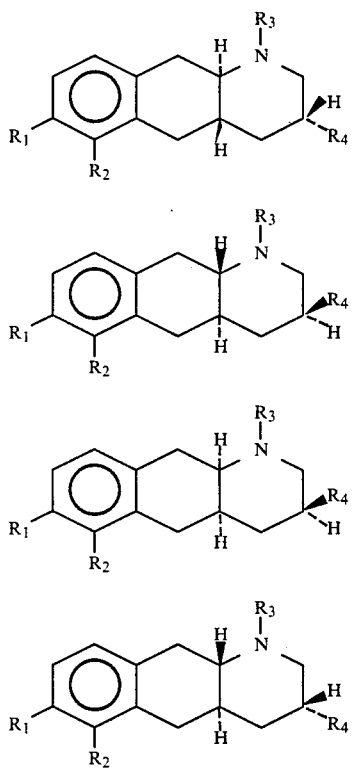

In relation to formula I the present invention includes the individual isomers, i.e. of formula Ia, Ib, Ic or Id, as well as mixtures thereof, especially racemates of formula Ia and Ib or Ic and Id.

For pharmaceutical application individual isomers and racemates of the compounds of the invention are preferred.

Racemic mixtures are identified throughout the present specification and claims by the name of one of the two enantiomers present (e.g. 3α, 4aα, 10aβ or 3β, 4aα, 10aβ), followed by the designation "(Racemate)".

In addition to the foregoing there is also provided a process for the production of the compounds of the invention in free or in salt form which process comprises:

(a) for the production of a 6- and/or 7-methoxy-trans-1,2,3,4,4a,5,10,10a-octahydro-benzo[g]quinoline, wherein the 1-position is unsubstituted and the 3-position is substituted by an amidated carboxy group, an optionally etherified hydroxymethyl group, a cyanomethyl group or an alkyl- or aryl-thiomethyl group or a physiologically-hydrolysable and -acceptable ester of a benzo[g]quinoline as aforesaid in which the 3-position is substituted by an esterified carboxy or esterified hydroxymethyl group, for example a compound of formula I¹,

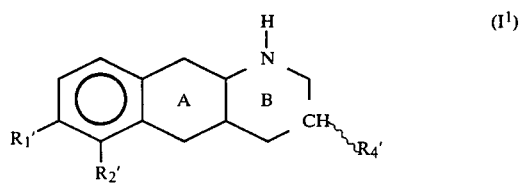

wherein
the rings A and B are trans-fused,
$R_1'$ and $R_2'$ are each independently hydrogen or methoxy, with the proviso that $R_1'$ and $R_2'$ may not both be hydrogen,
$R_4'$ is —CH$_2$OR$_5$, —CH$_2$CN, —CON(R$_6$)R$_7$ or —CH$_2$SR$_8$ or esterified —COOH or esterified —CH$_2$OH and
$R_5$, $R_6$, $R_7$ and $R_8$ have the meanings given for formula I, subjecting a corresponding 6- and/or 7-methoxy-trans-1,2,3,4,4a,5,10,10a-octahydro-benzo[g]quinoline or benzo[g]quinoline ester, wherein the 1-position is substituted by a benzyloxy or C$_{1-4}$alkoxy group, for example a compound of formula II,

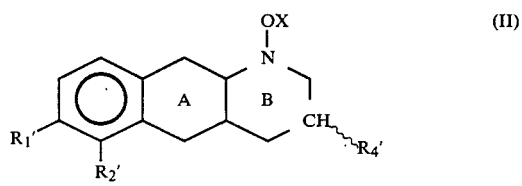

wherein the rings A and B are trans-fused, X is benzyl or C$_{1-4}$alkyl and $R_1'$, $R_2'$ and $R_4'$ have the meanings given for formula I¹, to cleavage, so as to split off the benzyloxy or C$_{1-4}$alkoxy group, e.g. the group —OX;

(b) for the production of a 6- and/or 7-methoxy-trans-1,2,3,4,4a,5,10,10a-octahydro-benzo[g]quinoline, wherein the 1-position is substituted, for example by a C$_{1-4}$alkyl group, and wherein the 3-position is substituted by an amidated carboxy group, an optionally etherified hydroxymethyl group, a cyanomethyl group or an alkyl- or arylthiomethyl group or a physiologically-hydrolysable and -acceptable ester of a benzo[g]quinoline as aforesaid in which the 3-position is substituted by an esterified carboxy or esterified hydroxymethyl group, for example a compound of formula I²,

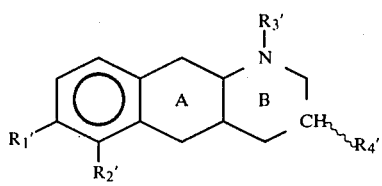
(I²)

wherein the rings A and B are trans-fused, $R_3'$ is $C_{1-4}$-alkyl and $R_1'$, $R_2'$ and $R_4'$ have the meanings given for formula $I^1$, introducing a substituent group into the 1-position of a corresponding 6- and/or 7-methoxy-trans-1,2,3,4,4a,5,10,10a-octahydro-benzo[g]quinoline or benzo[g]quinoline ester, wherein the 1-position is unsubstituted, e.g. by alkylation to introduce a $C_{1-4}$alkyl group, for example alkylating a compound of formula $I^1$ as defined above to introduce a $C_{1-4}$-alkyl group at the 1-position;

(c) for the production of 6- and/or 7-methoxy-trans-1,2,3,4,4a,5,10,10a-octahydro-benzo[g]quinoline, wherein the 3-position is substituted by a sulfamoylamino or carbamoylamino group, for example a compound of formula $I^3$,

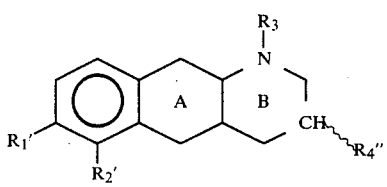
(I³)

wherein
the rings A and B are trans-fused,
$R_4''$ is $-NHSO_2N(R_9)R_{10}$ or $-NHCON(R_9)R_{10}$,
$R_3$, $R_9$ and $R_{10}$ have the meanings given for formula I and
$R_1'$ and $R_2'$ have the meanings given for formula $I^1$,
reacting the corresponding 6- and/or 7-methoxy-trans-1,2,3,4,4a,5,10,10a-octahydro-benzo[g]quinoline, wherein the 3-position is substituted by an amino ($-NH_2$) group, for example a compound of formula III,

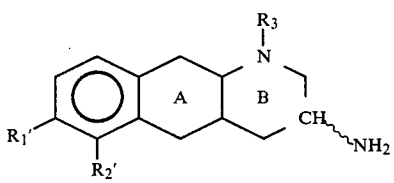
(III)

wherein the rings A and B are trans-fused and $R_1'$, $R_2'$ and $R_3$ are as defined for formula $I^3$, with an aminosulfonic or aminocarboxylic acid or reactive derivative thereof, e.g. with a compound of formula IVa or IVb,

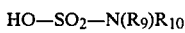
(IVa)

(IVb)

wherein $R_9$ and $R_{10}$ have the meanings given for formula I, or a reactive derivative thereof, (d) for the production of a 6- and/or 7-methoxy-trans-1,2,3,4,4a,5,10,10a-octahydro-benzo[g]quinoline, wherein the 3-position is substituted by a carboxy group, for example a compound of formula $I^4$,

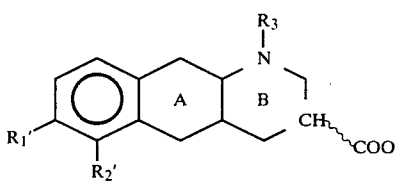
(I⁴)

wherein the rings A and B are trans-fused and wherein $R_1'$ and $R_2'$ have the meanings given for formula $I^1$ and $R_3$ has the meaning given for formula I, hydrolysing a corresponding 6- and/or 7-methoxy-trans-1,2,3,4,4a,5,10,10a-octahydro-benzo[g]quinoline, wherein the 3-position is substituted by an esterified carboxy group, for example a compound of formula V,

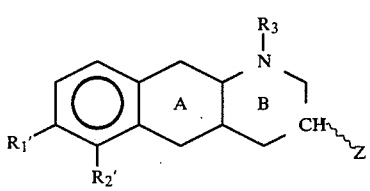
(V)

wherein the rings A and B are trans-fused, Z is an esterified carboxy group, and $R_1'$, $R_2'$ and $R_3$ are as defined above for formula $I^4$, (e) for the production of a 6- and/or 7-oxy-trans-1,2,3,4,4a,5,10,10a-octahydro-benzo[g]quinoline, in accordance with the invention and having at least one hydroxy group at the 6- and 7-positions, for example a compound of formula $I^5$,

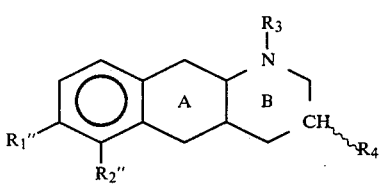
(I⁵)

wherein
the rings A and B are trans-fused,
$R_1''$ and $R_2''$ are each independently hydrogen, hydroxy or methoxy, with the proviso that at least one of $R_1''$ and $R_2''$ is hydroxy, and
$R_3$ and $R_4$ have the meanings given for formula I,
subjecting a corresponding 6- and/or 7-oxy-trans-1,2,3,4,4a,5,10,10a-octahydro-benzo[g]quinoline, having at least one methoxy group at the 6- and 7-positions, for example a compound of formula VI,

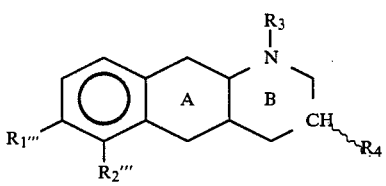
(VI)

wherein the rings A and B are trans-fused, $R_1'''$ and $R_2'''$ are each independently hydrogen, hydroxy or methoxy, with the proviso that at least one of $R_1'''$ and $R_2'''$ is methoxy, and $R_3$ and $R_4$ have the meanings given for formula I, to ether cleavage;

(f) for the production of a 6- and/or 7-oxy-trans-1,2,3,4,4a,5,10,10a-octahydro-benzo[g]quinoline wherein the 3-position is substituted by an amidated carboxy group, or of a physiologically-hydrolysable and -acceptable ester of a 6- and/or 7-oxy-trans-1,2,3,4,4a,5,10,10a-octahydro-benzo[g]quinoline in accordance with the invention, amidating a 6- and/or 7-oxy-trans-1,2,3,4,4a,5,10,10a-octahydro-benzo[g]quinoline wherein the 3-position is substituted by a carboxy group or a reactive derivative thereof, or acylating or esterifying a 6- and/or 7-oxy-trans-1,2,3,4,4a,5,10,10a-octahydro-benzo[g]quinoline in accordance with the invention and having one or more hydroxy and/or carboxy residues, e.g. at the 3-, 6- and/or 7-position or a reactive derivative thereof, for example reacting a benzo[g]quinoline of formula I as hereinbefore defined wherein $R_4$ is a carboxy group or a reactive derivative thereof with an amine of formula $HN(R_6)R_7$ wherein $R_6$ and $R_7$ have the meanings given for formula I, or reacting a benzo[g]quinoline of formula I as hereinbefore defined wherein at least one of the residues $R_1$, $R_2$ and $R_4$ is a hydroxy group (in the case of $R_1$ and $R_2$) or a hydroxymethyl group (in the case of $R_4$), or a benzo[g]quinoline of formula I as hereinbefore defined, wherein $R_4$ is a carboxy group or a reactive derivative thereof, with an appropriate acid or reactive derivative thereof, or with an appropriate alcohol;

and, recovering the benzo[g]quinoline or benzo[g]quinoline ester thus obtained in free or salt form.

Processes (a) to (f) above may be carried out in accordance with standard techniques known in the art.

For process (a) benzyloxy and $C_{1-4}$alkoxy groups at the 1-position, e.g. the group —OX of formula II, may be split off by reductive cleavage, e.g. by reduction in the presence of zinc and acetic acid.

Introduction of a substituent at the 1-position in accordance with process (b) may be carried out e.g. by alkylation or acylation. Introduction of a $C_{1-4}$alkyl group may be effected e.g. by direct alkylation, reductive alkylation or by acylation followed by reduction of the obtained amide.

Direct alkylation may be effected e.g. by reaction with a compound of formula $R_3'$-Q, wherein Q is a leaving group and $R_3'$ is $C_{1-4}$alkyl. Suitable leaving groups Q include chlorine, bromine and iodine as well as organic sulfonic acid residues such as methyl- and p-toluene-sulfonyloxy residues. The reaction is preferably carried out in the presence of an acid binding agent, for example an alkali-metal or alkaline-earth metal carbonate, and of an inert organic solvent or diluent such as dimethylformamide.

Reductive alkylation may be effected e.g. by reaction with an aldehyde of formula $R_3''CHO$, wherein $R_3''$ is hydrogen or $C_{1-3}$alkyl and with concomitant hydrogenation e.g. in the presence of an appropriate catalyst such as palladium on charcoal. The reaction is suitably carried out in the presence of an inert, organic solvent or diluent, for example the corresponding alcohol of formula $R_3''$—$CH_2OH$, with normal or slightly elevated pressure.

Alkylation by acylation and reduction can be effected e.g. by reaction with an acid halide of the formula $R_3''COHal$, wherein $R_3''$ has the meaning given above and Hal is chlorine or bromine, followed by reduction for example using $LiAlH_4$ or diborane as reducing agent.

Process (c) is carried out by acylation with an appropriate sulfamic or carbamic acid, for example a compound of formula IVa or IVb as defined above, or a reactive derivative thereof. Suitable reactive derivatives include the corresponding acid chlorides and bromides. The reaction is suitably carried out in the presence of an organic base such as triethylamine and in an inert, organic solvent or diluent such as chloroform, at normal or slightly elevated temperature.

Hydrolysis in accordance with process (d) may be effected by treatment with an appropriate alkali, or by acid hydrolysis for example in the presence of trifluoroacetic acid.

Ether cleavage in accordance with process (e) may be effected e.g. by reaction with HBr, $BBr_3$ or $NaSCH_3$, in the presence of an inert, organic solvent or diluent such as methylene dichloride or DMF. The reaction is suitably carried out at temperatures of from e.g. $-70°$ to $0°$ C. (HBr or $BBr_3$) or from $100°$ to reflux ($NaSCH_3$). Obtained hydroxy groups may readily be converted into other oxy substituents by techniques known in the art, e.g. by acylation in accordance with the following process (f).

Amidation or ester formation in accordance with process (f) may be carried out using any of the techniques known in the art, for example, where hydroxy groups are to be acylated, by reaction with a reactive derivative, e.g. the chloride or anhydride, of the selected acid or, where a carboxy group at the 3-position is to be amidated or esterified by reaction of e.g. a corresponding 3-carbonyl-halide or anhydride with the selected amide or alcohol.

The starting materials for use in the above processes, e.g. the compounds of formulae II, III, V and VI, exist in various isomeric forms corresponding to those hereinbefore described for the products of formula I. Each of the above processes may be carried out using starting materials in the form of one or other of the individual enantiomers, or in the form of mixtures, in particular racemic mixtures thereof. Conveniently the starting materials used are in racemic form. These may be produced in accordance with procedures as hereinafter described.

Where diastereomeric mixtures of the starting materials are used, the products too will be in the form of a diastereomeric mixture. Diastereomers may be separated, e.g. chromatographically to yield racemates free of diastereomeric contaminants. Obtained racemates may be resolved to obtain individual optically active enantiomers using known resolution techniques for example via formation of acid addition salts with optically active acids and resolution of the obtained diastereomeric salt.

The compounds of the invention may be recovered from the initially obtained reaction medium in free form or in salt form, e.g. in acid addition salt form. Alternatively initially obtained salts may be converted into the free form or vice versa.

Starting materials for process (a) may be obtained in accordance with known techniques, e.g. for the production of compounds of formula II in accordance with the following reaction sequence.

The starting materials of formula VII are known or may be produced analogously to known procedures.

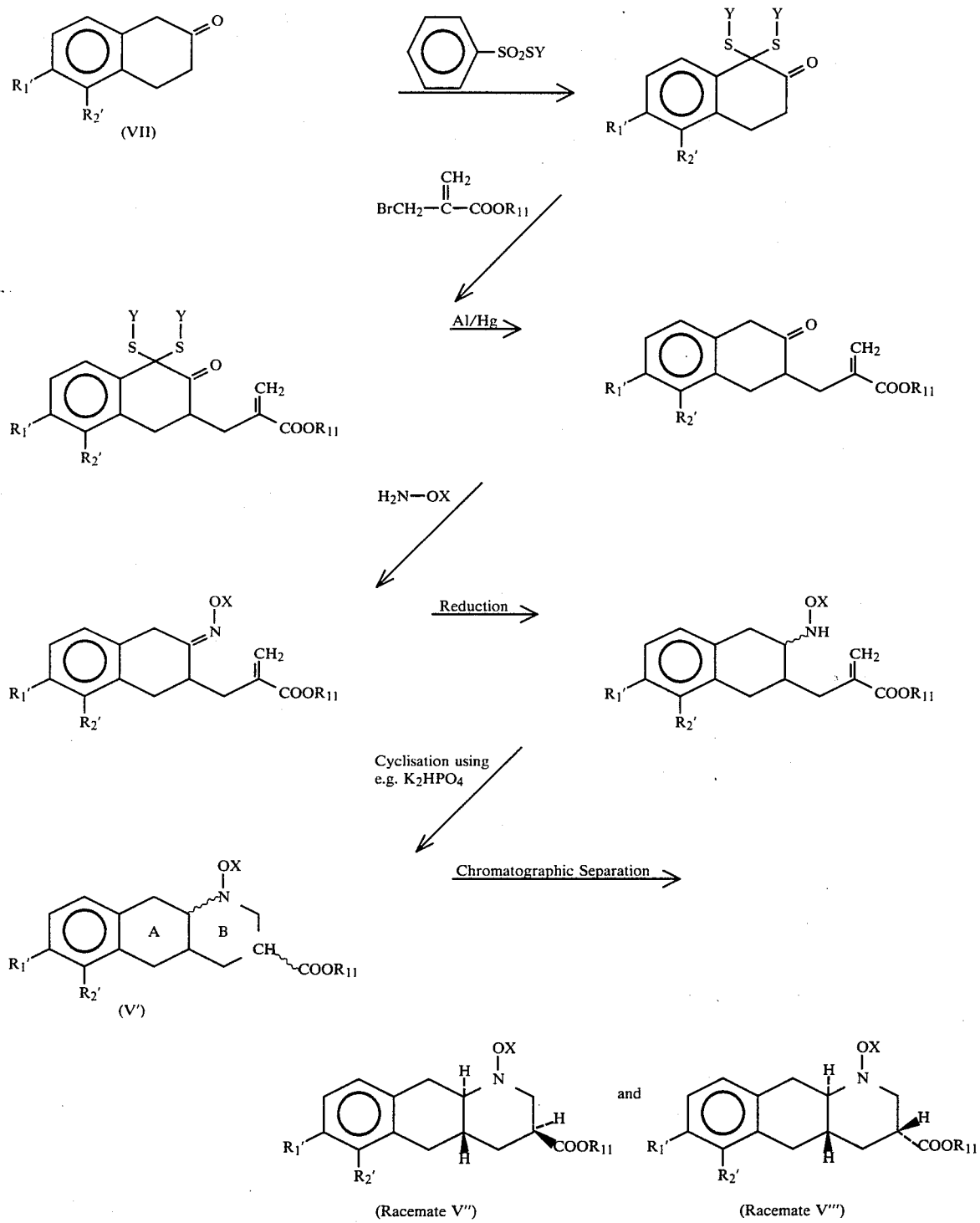

In the above reaction scheme $R_1'$, $R_2'$ and X have the meanings given hereinbefore for formula I', each Y is $C_{1-4}$alkyl or aryl (in particular phenyl) or both Ys together represent a $C_{3-4}$alkylene residue and $R_{11}$ is $C_{1-4}$alkyl (in particular methyl, iso-propyl or t.-butyl).

Each step in the above reaction scheme may be carried out in accordance with known techniques e.g. as hereinafter described in the accompanying examples.

As explained in example 1f, the initial product of the penultimate step (the compound of formula V', in which the rings A and B are cis- or trans-fused) contains only trace amounts of Racemate V'''. However, the amount of Racemate V''' present can readily be increased by epimerisation, e.g. in an alkaline medium as described e.g. in the following example (5a). For epimerisation $R_{11}$ is preferably methyl.

It will be appreciated that though isolation of racemates is conveniently carried out at the formula V′ stage, isolation may be effected at a later stage in synthesis, if desired. Similarly Racemates V″ and V‴ can be used directly for further reaction or can be resolved to yield individual enantiomers and further reactions carried out using the enantiomeric forms.

Compounds of formula V′, wherein the rings A and B are trans-fused are compounds of formula V as hereinbefore defined. When the residue —$COOR_{11}$ is a physiologically-hydrolysable and -acceptable ester residue, these compounds fall within the scope of formula II, as hereinbefore defined. The further compounds of formula II may be obtained from compounds of formula V by:

(i) reduction to obtain compounds of formula II, wherein $R_4'$ is —$CH_2OH$;

(ii) etherification of compounds obtained in accordance with (i) to obtain compounds of formula II, wherein $R_4'$ is —$CH_2OR_5$ and $R_5$ is $C_{1-4}$alkyl;

(iii) mesylation of compounds obtained in accordance with (i) to obtain corresponding compounds, wherein the substituent at the 3-position is $CH_3SO_2OCH_2$— and reaction of these with a compound of formula $R_8SH$ to obtain compounds of formula II, wherein $R_4'$ is —$CH_2SR_8$;

(iv) mesylation in accordance with (iii) and reaction of the product with an alkali-metal cyanide to obtain compounds of formula II, wherein $R_4'$ is —$CH_2CN$;

(v) amidation to obtain compounds of formula II, wherein $R_4'$ is —$CON(R_6)R_7$;

(vi) trans-esterification to obtain further compounds of formula II, wherein $R_4'$ is esterified —COOH; and (vii) acylation of compounds obtained in accordance with (i) to obtain compounds of formula II, wherein $R_4'$ is esterified —$CH_2OH$.

All of the reactions (i) to (vii) may be carried out in accordance with standard procedures e.g. as described in the accompanying examples.

Compounds of formula III as hereinbefore defined can be obtained from compounds of formula V in accordance with standard procedures, e.g. via Curtius reaction.

With the exception of the compounds of formula VII, all the intermediates hereinbefore described are new and are also part of the present invention.

It will further be appreciated that in addition to their pharmaceutical utility as hereinafter described, various of the compounds of formula I are also useful as intermediates for the production of further compounds of formula I. Thus the compounds of formula $I^1$, $I^2$ and $I^3$ may be used as starting materials for process (e) and the compounds of formula $I^4$ as starting materials for process (f).

The following examples are illustrative of the above described processes for the preparation of the compounds of the invention. In these examples, the following abbreviations are used:
DMF=Dimethylformamide
HMPT=Hexamethylphosphotriamide
MeOH=Methanol
EtOH=Ethanol
THF=Tetrahydrofuran
MS=Mass spectroscopy.

EXAMPLE 1

3α-Methoxycarbonyl-6-methoxy-1,2,3,4,4aα,5,10,10aβ-octahydro-benzo[g]quinoline (Racemate)

17 g of powdered zinc are added to a solution of 3.5 g 1-methoxy-3α-methoxycarbonyl-6-methoxy-1,2,3,4,4aα,5,10,10aβ-octahydro-benzo[g]quinoline (Racemate) in 35 ml acetic acid and 18 ml $H_2O$. The reaction mixture is stirred for ca. 15 hours at room temperature, and then filtered and concentrated. The residue is taken up in $CH_2Cl_2$, re-filtered and the residue washed with $CH_2Cl_2$. The filtrate is extracted using 1N $KHCO_3/H_2O$, the organic phase dried over $Na_2SO_4$ and evaporated, whereupon the title compound is obtained as a yellow oil. This crystallises on standing: M.P.=66°–68° C.

The starting material for the above process is obtained as follows:

(a) 1,1-Bis(phenylthio)-5-methoxy-2-tetralone:

70 g 5-methoxy-2-tetralone, 150 g benzenesulfonic acid S-phenyl ester and 120 g sodium acetate are stirred for 24 hours in 1,1 liter methanol at room temperature. The title compound precipitates out during the course of reaction and is recovered by concentrating the reaction mixture to ½ volume, cooling to 10° C. and filtering: M.P.=139°–141° C.

(b) β-[1,2,3,4-Tetrahydro-1,1-bis(phenylthio)-2-oxo-5-methoxy-3-naphthyl]-α-methylidene-propionic acid t.butylester:

12.6 ml diisopropylamine in 240 ml diethylether are added at −70° C. to 53 ml of a 1.6N solution of n-butyllithium in hexane. The mixture is left to warm for 15 minutes to −20° C. and is recooled to −90° C. 23.4 g of the product of step (a) dissolved in 250 ml THF/25 ml HMPT are then added drop-wise, so that the temperature does not rise above −70° C. After completion of addition, the reaction mixture is allowed to stand for 60 minutes at −70° C. and 19.8 g 2-bromo-methylacrylic acid t.butyl ester in 50 ml THF are added. The temperature is allowed to rise to −20° C. and an excess of 2N HCl is added. The obtained mixture is extracted by partitioning between $CH_2Cl_2/H_2O$ and the organic phase dried over $Na_2SO_4$ and evaporated to yield the title compound as a yellow oil, which is crystallised at −20° C. from diethyl ether/hexane: M.P.=120°–121° C.

(c) β-(1,2,3,4-Tetrahydro-2-oxo-5-methoxy-3-naphthyl)-α-methylidenepropionic acid t.butyl ester:

140 g of freshly amalgated aluminium filings are added to 100 g of the product of step (b) in 2.7 liters THF and 300 ml $H_2O$. The reaction mixture is warmed to 50° C. with stirring for 2 hours. The mixture is allowed to cool, and after addition of $CH_2Cl_2$, is filtered. The residue is washed several times with $CH_2Cl_2$, the filtrate evaporated and the residue extracted by partitioning between $CH_2Cl_2/H_2O$. The organic phase is dried over $Na_2SO_4$ and evaporated. The residue is re-crystallised at −20° C. from diethyl ether/hexane (preferably with seeding using previously obtained crystals) to yield the title compound: M.P.=95°–96° C.

(d) β-(1,2,3,4-Tetrahydro-2-methoxyimino-5-methoxy-3-naphthyl)-α-methylidene-propionic acid t.butyl ester:

79 g of the product of step (c), 41.5 g O-methylhydroxylamine hydrochloride and 44.5 g di-sodium-hydrogenphosphate bis-hydrate are stirred for 4 hours at room temperature in 1.6 liters methanol. The reaction mixture is evaporated and the residue extracted by partitioning between CH2Cl2/H2O. The organic phase is dried over Na2SO4, evaporated and the title compound re-crystallised from hexane: M.P.=72°-73° C.

(e) β-(1,2,3,4-Tetrahydro-2-methoxyamino-5-methoxy-3-naphthyl)-α-methylidene-propionic acid t.butyl ester:

52 g sodium cyanoborohydride are added to 60 g of the product of step (d) dissolved in 2.2 liters methanol. 7.5N HCl in methanol are added drop-wise, the pH being maintained during the course of reaction at 3 to 4. Reaction is completed after 22 hours. The pH is adjusted to 7 by the addition of buffer and the reaction mixture evaporated and extracted with CH2Cl2. The organic phase is dried over Na2SO4 and evaporated, whereupon the title compound is obtained as a diastereomeric mixture. Thin layer chromatographic analysis indicates that minor quantities of the step (f) products are already present.

(f) 1-Methoxy-3-t.butyloxycarbonyl-6-methoxy-1,2,3,4,4a,5,10,10a-octahydro-benzo[g]quinoline:

96.0 g potassium hydrogen phosphate are added to a solution of 61.0 g of the product of step (e) in 1.2 liters methanol. The reaction mixture is stirred for 3 days at room temperature, evaporated and the residue extracted by partitioning between CH2Cl2/H2O. The organic phases are dried over Na2SO4 and evaporated to yield the title compound as a brown oil. Thin layer chromatography indicates that the product is a diastereomeric mixture comprising four enantiomeric pairs. These are represented by the formulae A to D below, each of the four racemates being represented by the structure for one of the two enantiomers present:

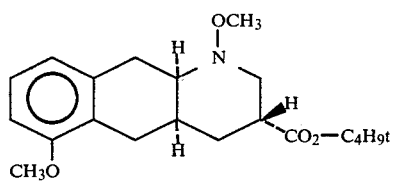

(Racemate) M.P. = 100-101° C.

(A)

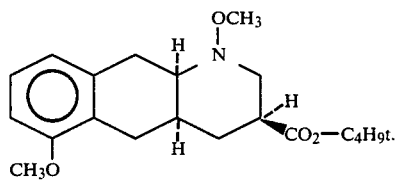

(Racemate) M.P. = 104-105° C.

(B)

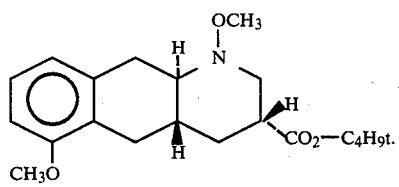

(Racemate) M.P. = 115-117° C.

(C)

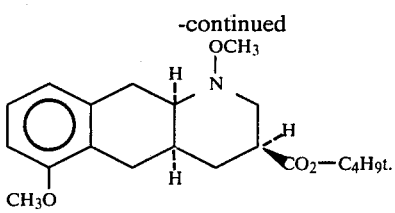

(Racemate) M.P. = 83-84° C.

(D)

The initially obtained diastereomeric mixture consists chiefly of racemates B and D, with only minor quantities of racemate A and only trace amounts of racemate C. The 4 racemates A through D are readily separated by medium pressure liquid chromatography.

(g) 1-Methoxy-3α-carboxy-6-methoxy-1,2,3,4,4aα,5,10,10aβ-octahydro-benzo[g]quinoline (Racemate):

4 g of racemate B obtained from step (f) are dissolved in 40 ml trifluoroacetic acid and the solution is allowed to stand for 75 minutes at room temperature. The reaction mixture is then concentrated and dried under high vacuum to yield the title compound as a grey solid which is then re-crystallised: M.P.=196°-197° C.

(h) 1-Methoxy-3α-methoxycarbonyl-6-methoxy-1,2,3,4,4aα,5,10,10aβ-octahydro-benzo[g]quinoline (Racemate):

An excess of diazomethane in diethylether is added to a solution of 6.6 g of the raw-product obtained in step (g) in 50 ml CH2Cl2. After concentration and evaporation of the obtained reaction mixture under high vacuum, the title compound is obtained as a brown solid. The raw product is employed directly for further reaction as hereinabove described. On re-crystallisation it has an M.P. of 111°-112° C.

EXAMPLE 2

1-n-Propyl-3α-methoxycarbonyl-6-methoxy-1,2,3,4,4aα,5,10,10aβ-octahydro-benzo[g]quinoline (Racemate):

3.0 g 3α-methoxycarbonyl-6-methoxy-1,2,3,4,4aα,5,10,10aβ-octahydro-benzo[g]quinoline (Racemate) (produced in accordance with example 1) are dissolved in 30 ml n-propanol. 3 ml n-propionaldehyde are added and hydrogenation is effected employing 1.2 g 10% palladium on charcoal with a reaction period of ca. 15 hours. The reaction mixture is filtered and evaporated, whereupon the title compound is obtained as a yellow oil which slowly solidifies: M.P.=81°-83° C.

EXAMPLE 3

1-n-Propyl-3α-diethylsulfamoylamino-6-methoxy-1,2,3,4,4aα,5,10,10aβ-octahydro-benzo[g]quinoline (Racemate):

1.5 g of 1-n-propyl-3α-amino-6-methoxy-1,2,3,4,4aα,5,10,10aβ-octahydro-benzo[g]quinoline (Racemate) and 3.0 ml triethylamine are added to a solution of 1.9 g diethylsulfamoyl chloride in 50 ml chloroform, and the reaction mixture is stirred for ca. 15 hours at 50° C. 50 ml 1N Na2CO3 solution are added and the mixture is stirred for 2 hours at room temperature, and extracted by partitioning between CH2Cl2/H2O. The organic phase is dried over Na2SO4, evaporated and purified chromatographically, to yield the title compound as a yellow oil, which is crystallised from diethyl ether/hexane at −20° C.: M.P.=88°-89° C.

The starting material for the above process is obtained as follows:

(a) 1-n-Propyl-3α-carbazoyl-6-methoxy-1,2,3,4,4aα,5,10,10aβ-octahydro-benzo[g]quinoline (Racemate):

18.5 ml hydrazine hydrate are added to a solution of 3.5 g 1-n-propyl-3α-methoxycarbonyl-6-methoxy-1,2,3,4,4aα,5,10,10aβ-octahydro-benzo[g]quinoline (Racemate) (produced in accordance with example 2) in 60 ml methanol and the reaction mixture is stirred for ca. 15 hours at 50° C. After concentration and drying under high vacuum, the residue is taken up in diethylether, dried over $Na_2SO_4$ and evaporated to yield the title compound as a yellow oil, which crystallises on standing: M.P.=84°–86° C.

(b) 1-n-Propyl-3α-amino-6-methoxy-1,2,3,4,4aα,5,10,10aβ-octahydro-benzo[g]quinoline (Racemate):

8 ml of a 1N solution of nitrosyl chloride in THF are added at −30° C. to a solution of 2.5 g of the product of step (a) in 80 ml THF. Reaction is completed within 5 minutes. The obtained reaction mixture is boiled under reflux for 1 hour, 50 ml 2N HCl are added, the solution is boiled for a further 2 hours under reflux, cooled, concentrated, the residue adjusted to pH 12 by the addition of 2N NaOH, and extracted with $CH_2Cl_2$. The organic phase is dried over $K_2CO_3$ and evaporated to yield the title compound as a brown oil. The product is used directly for further reaction as hereinabove described.

EXAMPLE 4

1-n-Propyl-3α-diethylsulfamoylamino-6-hydroxy-1,2,3,4,4aα,5,10,10aβ-octahydro-benzo[g]quinoline (Racemate)

2.7 ml borontribromide in 30 ml $CH_2Cl_2$ are added drop-wise at −30° C. to a solution of 1.9 g 1-n-propyl-3α-diethylsulfamoylamino-6-methoxy-1,2,3,4,4aα,5,10,10aβ-octahydro-benzo[g]quinoline (Racemate) (obtained in accordance with example 3) in 70 ml $CH_2Cl_2$. The reaction mixture is stirred for 4.5 hours at a temperature of from −30° C. to −10° C., 100 ml 1N $KHCO_3$ are added, the pH adjusted to 12 with 1N NaOH and the obtained mixture extracted several times with methylene chloride. The organic phases are washed until neutral with $H_2O$, dried over $Na_2SO_4$ and concentrated, whereupon a brown foam develops. This is taken up in 80 ml $CH_2Cl_2$/MeOH (1:1), 9 ml 7N HCl in $CH_3OH$ are added and the whole boiled for 15 minutes under reflux. The product is concentrated, extracted by partitioning between $CH_2Cl_2$/1N NaOH, the organic phase washed until neutral with $H_2O$, dried over $Na_2SO_4$ and evaporated. The solid residue is digested in boiling diethyl ether/hexane, cooled and filtered to yield the title compound as a beige powder: M.P.=122.5°–124° C.

EXAMPLE 5

3β-Methylthiomethyl-6-methoxy-1,2,3,4,4aα,5,10,10aβ-octahydro-benzo[g]quinoline (Racemate):

11.6 g zinc powder are added to a solution of 2.4 g 1-methoxy-3β-methylthiomethyl-6-methoxy-1,2,3,4,4aα,5,10,10aβ-octahydro-benzo[g]quinoline (Racemate) in 24 ml acetic acid and 12 ml $H_2O$. The reaction mixture is stirred for ca. 15 hours at room temperature, filtered and the filtrate concentrated. The residue is taken up in $CH_2Cl_2$ and filtered again. The filtrate is extracted with 1N $KHCO_3$ in $H_2O$, the organic phase dried and evaporated to yield the title compound: M.P.=107.5°–108.5° C.

The starting material is obtained as follows:

(a) 1-Methoxy-3β-methoxycarbonyl-6-methoxy-1,2,3,4,4aα,5,10,10aβ-octahydro-benzo[g]quinoline (Racemate):

8.5 g of 1-methoxy-3α-methoxycarbonyl-6-methoxy-1,2,3,4,4aα,5,10,10aβ-octahydro-benzo[g]quinoline (obtained in accordance with example 1h) are allowed to react for 2 days in a 1N solution of NaOH in MeOH/$H_2O$ (9:1) at room temperature. Reaction results in hydrolysis of the methoxycarbonyl group as well as partial epimerisation at the 3-position. The reaction mixture is concentrated, adjusted to pH 1–2 by addition of 4N HCl and extracted several times with $CH_2Cl_2/CH_3OH$ (95:5). The organic phase is dried and evaporated and the raw product reacted with an excess of diazomethane and evaporated. Epimerisation is completed by repeating the above procedure 2x, to yield the title compound, which is finally crystallised from ether/hexane: M.P.=108°–109° C.

(b) 1-Methoxy-3β-hydroxymethyl-6-methoxy-1,2,3,4,4aα,5,10,10aβ-octahydro-benzo[g]quinoline (Racemate):

A solution of 3.1 g of the product of step (a) in 50 ml THF is added to a suspension of 0.57 g lithium aluminium hydride in 50 ml THF at room temperature. The reaction mixture is stirred for a further 2 hours at room temperature and 0.6 ml $H_2O$, and 0.6 ml 20% NaOH followed by a further 2 ml $H_2O$ are added carefully. After 10 minutes the mixture is filtered and the filtrate evaporated to yield the title compound as a white powder: M.P.=149°–151° C.

(c) 1-Methoxy-3β-mesyloxymethyl-6-methoxy-1,2,3,4,4aα,5,10,10aβ-octahydro-benzo[g]quinoline (Racemate):

2.8 g of the product of step (b) in 40 ml pyridine are added to 1.6 ml methanesulfonyl chloride at 0° C. The mixture is allowed to stand for ca. 15 hours at room temperature, whereupon 20 ml of a 1N $NaHCO_3$ solution is added and the whole stirred for 30 minutes. The reaction mixture is concentrated and extracted by partitioning between $CH_2Cl_2/H_2O$. The organic phase is dried and evaporated and the residue crystallised from ethyl acetate to yield the title compound: M.P.=188°–189° C.

(d) 1-Methoxy-3β-methylthiomethyl-6-methoxy-1,2,3,4,4aα,5,10,10aβ-octahydro-benzo[g]quinoline (Racemate):

2.5 g sodium hydride (50% dispersion in oil) are added with ice-cooling to 4 ml methylmercaptan in 20 ml DMF. 3 g of the product of step (c) suspended in 30 ml DMF are then added at 0° C. and the reaction mixture stirred for a further 2 hours with ice-cooling. The reaction mixture is concentrated under high vacuum and the residue extracted by partitioning between $CH_2Cl_2/H_2O$. The organic phase is dried and evaporated whereupon the title compound is obtained. The product is used directly for further reaction as hereinabove described.

EXAMPLE 6

1-n-Propyl-3β-methylthiomethyl-6-methoxy-1,2,3,4,4aα,5,10,10aβ-octahydro-benzo[g]quinoline (Racemate):

0.87 ml n-propyl iodide and 1.9 g $K_2CO_3$ are added to 1.9 g of 3β-methylthiomethyl-6-methoxy- 1,2,3,4,4aα,5,10,10aβ-octahydro-benzo[g]quinoline (Racemate) (obtained in accordance with the process of example 5) dissolved in 20 ml DMF and the reaction mixture is stirred for ca. 15 hours at room-temperature, filtered and concentrated under high vacuum. The residue is extracted by partitioning between $CH_2Cl_2/H_2O$ and the organic phase dried and evaporated, whereupon the title compound is obtained as a yellow oil which crystallises on standing: M.P.=74°–75° C.

EXAMPLE 7

1-n-Propyl-3β-methylthiomethyl-6-hydroxy-1,2,3,4,4aα,5,10,10aβ-octahydro-benzo[q]quinoline (Racemate):

2.0 g of 1-n-propyl-3β-methylthiomethyl-6-methoxy-1,2,3,4,4aα,5,10,10aβ-octahydro-benzo[g]quinoline (Racemate) (obtained in accordance with the process of example 6) are dissolved in 100 ml $CH_2Cl_2$ and a solution of 3.6 ml boron tribromide in 30 ml $CH_2Cl_2$ are added drop-wise at −30° C. The reaction mixture is stirred for 5 hours at a temperature of from −30° to −10° C. 125 ml $KHCO_3$ are added, the pH adjusted to 12 by the addition of 2N NaOH, and the obtained mixture extracted several times with methylene chloride. The organic phases are washed until neutral with $H_2O$, dried over $Na_2SO_4$ and concentrated, whereupon a yellow precipitate develops. This is taken up in 100 ml $CH_2Cl_2/MeOH$ (1:1), 10 ml of a 7N solution of HCl in $CH_3OH$ are added and the obtained mixture boiled for 10 minutes under reflux. The product is concentrated and extracted by partitioning between $CH_2Cl_2/1N$ NaOH. The organic phase is washed until neutral, dried and evaporated. The solid residue is digested in diethylether and filtered off to yield the title compound as a beige powder: M.P.=173°–174° C.

EXAMPLE 8

3α-Methoxycarbonyl-7-methoxy-1,2,3,4,4aα,5,10,10aβ-octahydro-benzo[g]quinoline (Racemate):

The title compound is obtained analogously to example 1, proceeding via the following intermediates:
(a) 1,1-Bis(phenylthio)-6-methoxy-2-tetralone: M.P.=97°–99° C.
(b) β-[1,2,3,4-Tetrahydro-1,1-bis(phenylthio)-2-oxo-6-methoxy-3-naphthyl]-α-methylidene-propionic acid t.butyl ester: M.P.=118°–119° C.
(c) β-(1,2,3,4-Tetrahydro-2-oxo-6-methoxy-3-naphthyl)-α-methylidene-propionic acid t.butyl ester: M.P.=58°–60° C.
(d) β-(1,2,3,4-Tetrahydro-2-methoxyimino-6-methoxy-3-naphthyl)-α-methylidene-propionic acid t.butyl ester: yellow oil.
(e) β-(1,2,3,4-Tetrahydro-2-methoxyamino-6-methoxy-3-naphthyl)-α-methylidene-propionic acid t.butyl ester.
(f) 1-Methoxy-3-t.butyloxycarbonyl-7-methoxy-1,2,3,4,4a,5,10,10a-octahydro-benzo[g]quinoline as a diastereomeric mixture comprising 4 enantiomeric pairs as follows:
 (A) 1-Methoxy-3β-t.butyloxycarbonyl-7-methoxy-1,2,3,4,4aβ,5,10,10aβ-octahydro-benzo[g]quinoline (Racemate): M.P.=75° C.
 (B) 1-Methoxy-3α-t.butyloxycarbonyl-7-methoxy-1,2,3,4,4aα,5,10,10aβ-octahydro-benzo[g]quinoline (Racemate): M.P.=94° C.
 (C) 1-Methoxy-3β-t.butyloxycarbonyl-7-methoxy-1,2,3,4,4aα,5,10,10aβ-octahydro-benzo[g]quinoline (Racemate): M.P.=118° C.
 (D) 1-Methoxy-3α-t.butyloxycarbonyl-7-methoxy-1,2,3,4,4aβ,5,10,10aβ-octahydro-benzo[g]quinoline (Racemate): M.P.=91° C.

The initial diastereomeric mixture consists mainly of racemates B and D, with only minor quantities of A and trace amounts of C.

Individual racemates may readily be separated by medium pressure liquid chromatography.

Racemate B is used for further synthesis as follows:
(g) 1-Methoxy-3α-carboxy-7-methoxy-1,2,3,4,4aα,5,10,10aβ-octahydro-benzo[g]quinoline (Racemate).
(h) 1-Methoxy-3α-methoxycarbonyl-7-methoxy-1,2,3,4,4aα,5,10,10aβ-octahydro-benzo[g]quinoline (Racemate): M.P.=101°–103° C. (Starting material).

EXAMPLE 9

1-n-Propyl-3α-methoxycarbonyl-7-methoxy-1,2,3,4,4aα,5,10,10aβ-octahydro-benzo[g]quinoline (Racemate):

The title compound is produced analogously to example 2 starting from the product of example 8: MS: $M^+=317$.

EXAMPLE 10

1-n-Propyl-3α-diethylsulfamoylamino-7-methoxy-1,2,3,4,4aα,5,10,10aβ-octahydro-benzo[g]quinoline (Racemate):

The title compound is obtained as an oil analogously to example 3, starting from the product of example 9 via the following intermediates:
(a) 1-n-Propyl-3α-carbazoyl-7-methoxy-1,2,3,4,4aα,5,10,10aβ-octahydro-benzo[g]quinoline (Racemate): Oil.
(b) 1-n-Propyl-3α-amino-7-methoxy-1,2,3,4,4aα,5,10,10aβ-octahydro-benzo[g]quinoline (Racemate).

EXAMPLE 11

1-n-Propyl-3α-diethylsulfamoylamino-7-hydroxy-1,2,3,4,4aα,5,10,10aβ-octahydro-benzo[g]quinoline (Racemate):

The title compound is obtained analogously to example 4, starting from the product of example 10: M.P. for the hydrochloride=210°–211° C.

EXAMPLE 12

3β-Methylthiomethyl-7-methoxy-1,2,3,4,4aα,5,10,10aβ-octahydro-benzo[g]quinoline (Racemate).

The title compound is obtained analogously to example 5 as an oil via the following intermediates starting from the product of example (8h):
(a) 1-Methoxy-3β-methoxycarbonyl-7-methoxy-1,2,3,4,4aα,5,10,10aβ-octahydro-benzo[g]quinoline (Racemate): M.P.=74°–76° C.
(b) 1-Methoxy-3β-hydroxymethyl-7-methoxy-1,2,3,4,4aα,5,10,10aβ-octahydro-benzo[g]quinoline (Racemate).
(c) 1-Methoxy-3β-mesyloxymethyl-7-methoxy-1,2,3,4,4aα,5,10,10aβ-octahydro-benzo[g]quinoline (Racemate).
(d) 1-Methoxy-3β-methylthiomethyl-7-methoxy-1,2,3,4,4aα,5,10,10aβ-octahydro-benzo[g]quinoline (Racemate): M.P.=92°–94° C.

EXAMPLE 13

1-n-Propyl-3β-methylthiomethyl-7-methoxy-1,2,3,4,4aα,5,10,10aβ-octahydro-benzo[g]quinoline (Racemate):

The title compound is obtained analogously to example 6, starting from the product of example 12: M.P. for the hydrochloride = 236°–238° C.

EXAMPLE 14

1-n-Propyl-3β-methylthiomethyl-7-hydroxy-1,2,3,4,4aα,5,10,10aβ-octahydro-benzo[g]quinoline (Racemate):

4 g of a 50% dispersion of sodium hydride in oil are washed several times with hexane and suspended in 50 ml DMF. 12 ml methylmercaptan are then added portion-wise, followed by 3.5 g of 1-n-propyl-3β-methylthiomethyl-7-methoxy-1,2,3,4,4aα,5,10,10aβ-octahydro-benzo[g]quinoline (obtained in accordance with example 13), dissolved in a little DMF.

The reaction mixture is stirred for 5 hours at 160° C., cooled and the DMF removed under high vacuum. The residue is taken up in methylene chloride and extracted 2x, first using 2N HCl and then saturated NaHCO$_3$. The obtained solution is dried over Na$_2$SO$_4$, evaporated, purified chromatographically and the main fraction re-crystallised from CH$_2$Cl$_2$/hexane to yield the title compound: M.P. = 132°–134° C.

EXAMPLE 15

3β-Methoxycarbonyl-6-methoxy-1,2,3,4,4aα,5,10,10aβ-octahydro-benzo[g]quinoline (Racemate)

60 g of zinc powder are added to a solution of 12.2 g 1-methoxy-3β-methoxycarbonyl-6-methoxy-1,2,3,4,4aα,5,10,10aβ-octahydro-benzo[g]quinoline (Racemate) (Example 5a) in 180 ml acetic acid/H$_2$O (2:1) and the reaction mixture is stirred for 3 days at room temperature. Isolation of the product is carried out analogously to example 1 to yield the title compound.

EXAMPLE 16

1-Methyl-3β-methoxycarbonyl-6-methoxy-1,2,3,4,4aα,5,10,10aβ-octahydro-benzo[g]quinoline (Racemate)

56 ml aqueous formaldehyde solution (35%) are added to a solution of 10 g of the product of example 15 in 180 ml methanol and the reaction mixture is hydrogenated for ca. 15 hours using 2 g Pd on charcoal as catalyst. The product is filtered, the filtrate concentrated and the residue extracted by partitioning between CH$_2$Cl$_2$/1N KHCO$_3$ solution. The organic phase is dried over Na$_2$SO$_4$ and evaporated to yield the title compound: M.P. subsequent to re-crystallisation = 93°–94° C.

EXAMPLE 17

1-Methyl-3β-methoxycarbonyl-6-hydroxy-1,2,3,4,4aα,5,10,10aβ-octahydro-benzo[g]quinoline (Racemate)

A solution of 2.4 ml borontribromide in 20 ml CH$_2$Cl$_2$ are added dropwise at −20° C. to a solution of 1.2 g of the product of example 16 in 100 ml CH$_2$Cl$_2$, and the reaction mixture is stirred for 8 hours at −5° to −10° C. 50 ml H$_2$O are added and the temperature allowed to rise to room temperature. The obtained suspension is filtered, the residue boiled for 1 hour in 50 ml of a 1N solution of HCl in MeOH and evaporated. The residue is partitioned between CH$_2$Cl$_2$/2N Na$_2$CO$_3$ solution, the organic phase washed with water until neutral, dried over Na$_2$SO$_4$ and evaporated to yield the title compound as an amorphous powder: M.P. = 182° C.

EXAMPLE 18

1-Methyl-3β-carboxy-6-hydroxy-1,2,3,4,4aα,5,10,10aβ-octahydro-benzo[g]quinoline (Racemate)

7.5 ml of a 1N solution of KOH in EtOH is added to a solution of 0.7 g of the product of example 17 in 10 ml EtOH and the reaction solution boiled for 1 hour under reflux. After cooling the reaction mixture is neutralised by the addition of 7.5 ml of a 1N HCl solution in MeOH and evaporated. The residue is suspended in 2 ml H$_2$O. The non-soluble portion is separated by filtration to yield the title compound M.P. = 250°–260° C. (with decomposition).

EXAMPLE 19

6-Hydroxy-N-(2-methoxy-5-pyridyl)-1-methyl-1,2,3,4,4aα,5,10,10aβ-octahydro-benzo[g]quinoline-3β-carboxamide (Racemate)

A solution of 1.35 ml trifluoroacetic acid anhydride and 0.6 ml trifluoroacetic acid in 7 ml acetonitrile are added at −20° C. to a suspension of 1.4 g of the product of example 18 in 35 ml acetonitrile, whereupon dissolution of the suspended material occurs. The reaction mixture is stirred for 40 minutes at 0° C., re-cooled to −20° C. and 1.4 g 5-amino-2-methoxypyridine dissolved in 12 ml pyridine are added. The obtained reaction mixture is then stirred for a further 4 hours at 0° C. The obtained solution is partitioned between CH$_2$Cl$_2$/H$_2$O, the organic phases dried over Na$_2$SO$_4$ and evaporated (insoluble, unreacted starting material being recovered subsequent to partitioning by filtration). The residue is purified chromatographically to yield the title compound: M.P. = 209°–211° C.

EXAMPLE 20

3β-Methoxycarbonyl-7-methoxy-1,2,3,4,4aα,5,10,10aβ-octahydro-benzo[g]quinoline (Racemate)

The title compound is obtained analogously to example 15 starting from the product of example 12 (a): M.P. = 110° C.

EXAMPLE 21

1-Methyl-3β-methoxycarbonyl-7-methoxy-1,2,3,4,4aα,5,10,10aβ-octahydro-benzo[g]quinoline (Racemate)

The title compound is obtained analogously to example 16 starting from the product of example 20.

EXAMPLE 22

1-Methyl-3β-methoxycarbonyl-7-hydroxy-1,2,3,4,4aα,5,10,10aβ-octahydro-benzo[g]quinoline (Racemate)

The title compound is obtained analogously to example 17 starting from the product of example 21: M.P. = 197°–199° C.

EXAMPLE 23

1-Methyl-3β-carboxy-7-hydroxy-1,2,3,4,4aα,5,10,10aβ-octahydro-benzo[g]quinoline (Racemate)

The title compound is obtained analogously to example 18 starting from the product of example 22: M.P.=194°–196° C.

EXAMPLE 24

7-Hydroxy-N-(2-methoxy-5-pyridyl)-1-methyl-1,2,3,4,4aα,5,10,10aβ-octahydro-benzo[g]quinoline-3β-carboxamide (Racemate)

The title compound is obtained analogously to example 19 starting from the product of example 23: M.P.=244°–246° C.

EXAMPLE 25

1-n-Propyl-3α-diethylsulfamoylamino-6-benzoyloxy-1,2,3,4,4aα,5,10,10aβ-octahydro-benzo[g]quinoline (Racemate)

4.4 ml benzoylchloride are added drop-wise at 0° C. to a solution of 1.5 g of the product of example 4 in 200 ml pyridine. The reaction mixture is stirred for 1 hour with ice-cooling, and then concentrated, and the residue partitioned between $CH_2Cl_2/H_2O$. The organic phase is dried over $Na_2SO_4$ and evaporated and the residue recrystallised in the form of the hydrochloride salt from ether: M.P.=166°–168° C.

The benzo[g]quinoline end-products of the present invention in particular the benzo[g]quinolines of formula I, as well as the pharmaceutically acceptable salts thereof possess valuable pharmaceutical properties as indicated in animal tests and are accordingly useful as pharmaceuticals.

In particular they exhibit prolactin secretion inhibiting activity as indicated by inhibition of pregnancy (ovum implantation) on administration to female rats on the 5th day after insemination, at dosages of from 0.01 to 3.0 mg/kg s.c., as well as by reduction of serum prolactin levels as measured by RIA, 4 hours after administration to male rats at dosages of from 0.001 to 0.1 mg/kg s.c. [both tests carried out in accordance with the methods described in *Experientia* 34, 1330 (1978)].

The said benzo[g]quinolines and salts are accordingly useful as prolactin secretion inhibitors, e.g. in the treatment of conditions or disorders for which reduction of prolactin secretion levels is indicated, for example for the treatment of galactorrhoea including post-partum galactorrhoea, for the treatment of prolactin-dependent menstrual disorders including amenorrhoea, for the inhibition of lactation including post-partum lactation and morbid lactation as well as for the treatment of hyperprolactinaemic hypogonadism in males and females and of prolactinoma.

For this use the dosage will of course vary depending on e.g. the particular compound employed, the mode of administration, the particular condition to be treated and the effect desired. However, in general satisfactory results are obtained on administration at daily dosages of from about 0.004 to about 0.15 mg/kg body weight, conveniently given in divided doses 2 to 4 times a day or in sustained release form. For larger mammals, the total daily dosage is in the range of from about 0.25 to about 10 mg and suitable unit dosage forms, e.g. for oral administration, comprise from about 0.05 to about 5 mg of active ingredient in free or pharmaceutically acceptable salt form together with a pharmaceutically acceptable diluent or carrier therefor.

As already indicated the daily dosages suitable for any particular compound will depend on a number of factors including its relative potency of activity. For the compound of example 4, which is the most preferred compound in accordance with the present invention, the determined $ED_{50}$ in the ovum implantation test described above is 0.02 mg/kg. For the known prolactin secretion inhibitor bromocriptine, a determined $ED_{50}$ in the same test is 0.75 mg/kg. An indicated daily dosage for the compound of example 4 would accordingly be of the order of from about 1/30 to about 1/10 of the daily dosage applicable in the case of bromocriptine.

In addition to the foregoing the benzo[g]quinoline end-products of the present invention in particular the benzo[g]quinolines of formula I, as well as the pharmaceutically acceptable salts thereof also exhibit dopaminergic activity as indicated by elicited contralateral rotation on administration at dosages of from 0.05 to 2.0 mg/kg i.p. to rats in which unilateral damage of the nigro-neostriatal dopamine pathway has been induced by injection of 6-hydroxydopamine into the substantia nigra [test carried out in accordance with the method of U. Ungerstedt, *Acta. physiol. scand. Suppl.* 367, 69–93 (1973)]. The said compounds also exhibit stereotopy in the apomorphine stereotypy test on administration at dosages of about 10 mg/kg i.p..

The said benzo[g]quinolines and salts are accordingly also useful as dopaminergic agents e.g. for the treatment of Morbus Parkinson. For this use the dosage will of course vary depending on e.g. the particular compound employed, the mode of administration, the condition to be treated and the effect desired. However, in general satisfactory results are obtained on administration at daily dosages of from about 0.01 to about 0.5 mg/kg body weight, conveniently given in divided doses 2 to 4 times a day or in sustained release form. For larger mammals, the total daily dosage is in the range of from about 1 to about 40 mg and suitable unit dosage forms, e.g. for oral administration comprise from about 0.25 to about 20 mg of active ingredient in free or pharmaceutically acceptable salt form together with a pharmaceutically acceptable diluent or carrier therefor.

The benzo[g]quinoline end-products of the invention in particular the benzo[g]quinolines of formula I, as well as the pharmaceutically acceptable acid addition salts thereof also exhibit dopamine receptor stimulating activity as indicated by induction of decreased blood pressure and decreased superior mesenteric and renal vascular resistance in the anaesthetised dog. For this test dogs are employed which have been anaesthetised with nembutal. Blood pressure is measured by means of a catheter inserted in the femoral artery and heart-frequency is monitored by means of an electrocardiogram. A submaximal isoprenalin dosage (0.5 µg/mg) is administered 3× i.v. and blood pressure and heart frequency is measured. The test substance is administered by injection into the femoral vein 10 minutes after the 3rd isoprenaline dosage and the inhibition of isoprenalin induced tachycardia is determined following repeated isoprenalin administrations at the same dosage after a further 5, 15, 35, 75, 155 and 315 minutes, with a follow-up measurement of heart frequency and blood pressure. The said compounds of the invention cause a decrease in blood pressure as well as a decrease in superior mesenteric and renal vascular resistance on administration in the above test at doses of from 2.5 to 100 µg/kg i.v.

The said benzo[g]quinolines and salts are accordingly also useful as dopamine receptor stimulators e.g. for the treatment or prophylaxis of coronary disease, e.g. of congestive heart failure, as well as of hypertension and oliguric renal failure. For this use the dosage will of course vary depending on e.g. the particular compound employed, the mode of administration, the condition to be treated and the effect desired. However, in general satisfactory results are obtained on administration at daily dosages of from about 0.02 to about 10 mg/kg body weight conveniently given in divided doses 2 to 4 times a day or in sustained release form. For larger mammals, the total daily dosage is in the range of from about 1 to 500 mg and suitable unit dosage forms e.g. for oral administration comprise from about 0.25 to 250 mg of active ingredient in free or pharmaceutically acceptable salt form together with a pharmaceutically acceptable diluent or carrier therefor.

As indicated above for administration the benzo[g]quinolines may be in free or in pharmaceutically acceptable salt form, in particular pharmaceutically acceptable acid addition salt form. Such salt forms exhibit the same order of activity as the free forms.

In accordance with the foregoing the present invention also provides:

1. A 6- and/or 7-oxy-trans-1,2,3,4,4a,5,10,10a-octahydro-benzo[g]quinoline in which the 3-position is substituted by an optionally amidated carboxy group, an optionally etherified hydroxymethyl group, a cyanomethyl group, an alkyl- or arylthiomethyl group or a sulfamoylamino or carbamoylamino group, in particular a benzo[g]quinoline of formula I as hereinbefore defined, or a physiologically-hydrolysable and -acceptable ester thereof, in free or pharmaceutically acceptable salt form for use as:
   1.1 a prolactin secretion inhibitor, in particular
      1.1.1 for use in the treatment of galactorrhoea, premenstrual disorders, hyperprolactinaemic hypogonadism or prolactinoma or for use as a lactation inhibitor;
   1.2 a dopaminergic agent, in particular
      1.2.1 for use as in the treatment of Morbus Parkinson; and
   1.3 as a dopamine receptor stimulating agent, in particular
      1.3.1 for the treatment or prophylaxis of coronary disease, especially congestive heart failure, as well as for the treatment of hypertension or oliguric renal failure;
2. A method of treating conditions or disorders having an aetiology comprising or associated with prolactin secretion, in particular a condition or disorder as specified under 1.1.1 above, or a method of treating Morbus Parkinson, or a method for the prophylaxis or treatment of a condition or disorder as specified under 1.3.1 above, in a subject in need of such treatment, which method comprises administering to said subject an effective amount of a benzo[g]quinoline, ester or salt as defined under 1. above; as well as
3. A pharmaceutical composition comprising a benzo[g]quinoline, ester or salt as defined under 1. above, together with a pharmaceutically acceptable diluent or carrier therefore.

Pharmaceutical compositions in accordance with 3. above may be prepared employing conventional techniques known in the galenic art. Suitable galenic forms for administration include e.g. tablets and capsules.

We claim:

1. A benzo[g]quinoline of formula I,

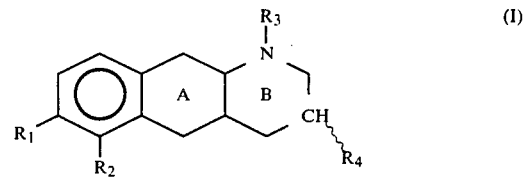

(I)

wherein
the rings A and B are trans-fused and wherein
$R_1$ and $R_2$ are each independently hydrogen, hydroxy or methoxy, with the proviso that $R_1$ and $R_2$ may not both be hydrogen;
$R_3$ is hydrogen or $C_{1-4}$alkyl;
$R_4$ is —COOH, —CH$_2$OR$_5$, —CH$_2$CN, —CON(R$_6$)R$_7$, —CH$_2$SR$_8$, —NHSO$_2$N(R$_9$)R$_{10}$ or —NHCON(R$_9$)R$_{10}$,
$R_5$ is hydrogen or $C_{1-3}$alkyl,
$R_6$ is hydrogen or $C_{1-3}$alkyl and
$R_7$ is hydrogen, $C_{1-3}$alkyl, phenyl or pyridyl, said phenyl or pyridyl being optionally substituted by halogen, methyl or methoxy or
$R_6$ and $R_7$ together are —(CH$_2$)$_4$—, —(CH$_2$)$_5$— or —(CH$_2$)$_2$—O—(CH$_2$)$_2$—,
$R_8$ is $C_{1-4}$alkyl or pyridyl, said pyridyl being optionally substituted by halogen, methyl or methoxy, and
$R_9$ and $R_{10}$ are each independently hydrogen or $C_{1-3}$alkyl or together are —(CH$_2$)$_4$— or —(CH$_2$)$_5$—,
or a physiologically-hydrolysable and -acceptable ester thereof, in free or in pharmaceutically acceptable salt form.

2. A benzo[g]quinoline according to claim 1 of the formula

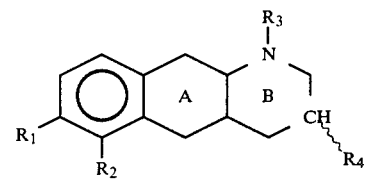

wherein
one of $R_1$ and $R_2$ is hydrogen and the other is hydroxy,
$R_3$ is n-propyl,
$R_4$ is —NHSO$_2$N(R$_9$)R$_{10}$,
$R_9$ is ethyl and
$R_{10}$ is ethyl,
or a physiologically-hydrolysable and -acceptable ester thereof, in free base form or in pharmaceutically acceptable salt form.

3. A benzo[g]quinoline according to claim 2 of the formula

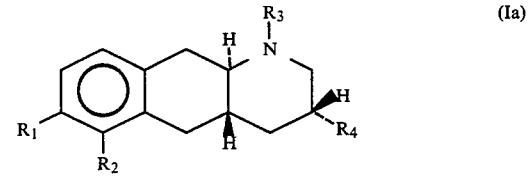

(Ia)

where $R_1$, $R_2$, $R_3$, $R_4$ are as defined in claim 17.

4. A compound according to claim 1 in the form of a racemate.

5. 1-n-Propyl-3α-diethylsulfamoylamino-6-hydroxy-1,2,3,4,4α,5,10,10aβ-octahydro-benzo[g]quinoline (Racemate) according to claim 1.

6. A compound according to claim 1 selected from the group comprising:

3β-Methylthiomethyl-7-methoxy-1,2,3,4,4aα,5,10,-10aβ-octahydro-benzo[g]quinoline (Racemate);

1-n-Propyl-3β-methylthiomethyl-7-methoxy-1,2,3,4,4aα,5,10,10aβ-octahydro-benzo[g]quinoline (Racemate); and 1-n-Propyl-3β-methylthiomethyl-7-hydroxy-1,2,3,4,4aα,5,10,10aβ-octahydro-benzo[g]quinoline (Racemate).

7. A compound according to claim 1 selected from the group comprising:

3α-Methoxycarbonyl-6-methoxy-1,2,3,4,4aα,5,10,10aβ-octahydro-benzo[g]quinoline (Racemate);

1-n-Propyl-3α-methoxycarbonyl-6-methoxy-1,2,3,4,4aα,5,10,10aβ-octahydro-benzo[g]quinoline (Racemate);

1-n-Propyl-3α-diethylsulfamoylamino-6-methoxy-1,2,3,4,4aα,5,10,10aβ-octahydro-benzo[g]quinoline (Racemate);

3β-Methylthiomethyl-6-methoxy-1,2,3,4,4aα,5,10,-10aβ-octahydro-benzo[g]quinoline (Racemate);

1-n-Propyl-3β-methylthiomethyl-6-methoxy-1,2,3,4,4aα,5,10,10aβ-octahydro-benzo[g]quinoline (Racemate);

1-n-Propyl-3β-methylthiomethyl-6-hydroxy-1,2,3,4,4aα,5,10,10aβ-octahydro-benzo[g]quinoline (Racemate);

3α-Methoxycarbonyl-7-methoxy-1,2,3,4,4aα,5,10,10aβ-octahydro-benzo[g]quinoline (Racemate);

1-n-Propyl-3α-methoxycarbonyl-7-methoxy-1,2,3,4,4aα,5,10,10aβ-octahydro-benzo[g]quinoline (Racemate);

1-n-Propyl-3α-diethylsulfamoylamino-7-methoxy-1,2,3,4,4aα,5,10,10aβ-octahydro-benzo[g]quinoline (Racemate);

1-n-Propyl-3α-diethylsulfamoylamino-7-hydroxy-1,2,3,4,4aα,5,10,10aβ-octahydro-benzo[g]quinoline (Racemate); and 7-Hydroxy-N-(2-methoxy-5-pyridyl)-1-methyl-1,2,3,4,4aα,5,10,10aβ-octahydro-benzo[g]quinoline-3β-carboxamide (Racemate).

8. A compound according to claim 1 selected from the group comprising:

3β-Methoxycarbonyl-6-methoxy-1,2,3,4,4aα,5,10,10aβ-octahydro-benzo[g]quinoline (Racemate);

1-Methyl-3β-methoxycarbonyl-6-methoxy-1,2,3,4,4aα,5,10,10aβ-octahydro-benzo[g]quinoline (Racemate);

1-Methyl-3β-methoxycarbonyl-6-hydroxy-1,2,3,4,4aα,5,10,10aβ-octahydro-benzo[g]quinoline (Racemate);

1-Methyl-3β-carboxy-6-hydroxy-1,2,3,4,4aα,5,10,10aβ-octahydro-benzo[g]quinoline (Racemate);

6-Hydroxy-N-(2-methoxy-5-pyridyl)-1-methyl-1,2,3,4,4aα,5,10,10aβ-octahydro-benzo[g]quinoline-3β-carboxamide (Racemate);

3β-Methoxycarbonyl-7-methoxy-1,2,3,4,4aα,5,10,10aβ-octahydro-benzo[g]quinoline (Racemate);

1-Methyl-3β-methoxycarbonyl-7-methoxy-1,2,3,4,4aα,5,10,10aβ-octahydro-benzo[g]quinoline (Racemate);

1-Methyl-3β-methoxycarbonyl-7-hydroxy-1,2,3,4,4aα,5,10,10aβ-octahydro-benzo[g]quinoline (Racemate);

1-Methyl-3β-carboxy-7-hydroxy-1,2,3,4,4aα,5,10,10aβ-octahydro-benzo[g]quinoline (Racemate); and 1-n-Propyl-3α-diethylsulfamoylamino-6-benzoyloxy-1,2,3,4,4aα,5,10,10aβ-octahydro-benzo[g]quinoline (Racemate).

9. A pharmaceutical composition for use in inhibiting prolactin secretion, treating Morbus Parkinson or in the treatment or prophylaxis of coronary disease, hypertension or oliguric renal failure comprising a pharmaceutically effective amount of a compound according to claim 1 in free or in pharmaceutically acceptable salt form, together with a pharmaceutically acceptable diluent or carrier therefor.

10. A method of inhibiting prolactin secretion in a subject in need of such treatment which method comprises administering to said subject an effective amount of a compound according to claim 1 in free or in pharmaceutically acceptable salt form.

11. A method according to claim 10 for the treatment of galactorrhoea, premenstrual disorders, hyperprolactinaemic hypogonadism or prolactinoma or for the inhibition of lactation.

12. A method of treating Morbus Parkinson in a subject in need of such treatment, which method comprises administering to said subject an effective amount of a compound according to claim 1 in free or in pharmaceutically acceptable salt form.

13. A method for the treatment or prophylaxis of coronary disease, hypertension or oliguric renal failure in a subject in need of such treatment, which method comprises administering to said subject an effective amount of a compound according to claim 1 in free or in pharmaceutically acceptable salt form.

14. A benzo[g]quinoline according to claim 2 in the form of a racemate.

15. A benzo[g]quinoline according to claim 2 of the formula

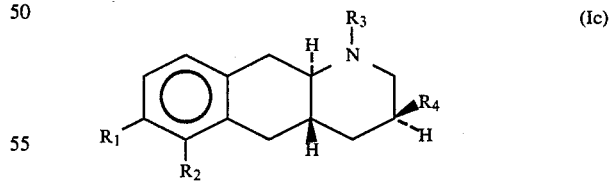

where $R_1$, $R_2$, $R_3$ and $R_4$ are as defined in claim 2.

16. A benzo[g]quinoline according to claim 15 in the form of a racemate.

* * * * *